United States Patent
Lopez Alvarez et al.

(10) Patent No.: US 9,016,145 B2
(45) Date of Patent: Apr. 28, 2015

(54) DEVICE FOR THE AUTOMATIC TAKING OF SAMPLES OF LIQUID FROM COLLECTION CONTAINERS AND METHOD FOR PERFORMING SAID SAMPLE TAKING

(75) Inventors: Diego Lopez Alvarez, La Garriga (ES); Sergi Roura Adell, Arenys de Munt (ES); Francisco Rodriguez Garcia, Terrassa (ES); Oriol Causi Casamor, Barcelona (ES); Shinji Wada, Arcadia, CA (US)

(73) Assignee: Grifols, S.A., Barcelona (ES)

( * ) Notice: Subject to any disclaimer, the term of this patent is extended or adjusted under 35 U.S.C. 154(b) by 1012 days.

(21) Appl. No.: 12/689,607

(22) Filed: Jan. 19, 2010

(65) Prior Publication Data

US 2010/0180698 A1    Jul. 22, 2010

(30) Foreign Application Priority Data

Jan. 19, 2009   (ES) .................................. 200900138

(51) Int. Cl.
*G01N 1/22* (2006.01)
*B60R 13/10* (2006.01)
*G01N 35/00* (2006.01)
*G01N 35/04* (2006.01)

(52) U.S. Cl.
CPC ............ *B60R 13/10* (2013.01); *G01N 35/0099* (2013.01); *G01N 2035/00861* (2013.01); *G01N 2035/0406* (2013.01)

(58) Field of Classification Search
CPC .................................. G01N 1/00; G01N 1/18

USPC ........................................................ 73/863.01
See application file for complete search history.

(56) References Cited

U.S. PATENT DOCUMENTS

| | | | |
|---|---|---|---|
| 4,872,353 A * | 10/1989 | Orr et al. ..................... | 73/863.01 |
| 5,020,297 A * | 6/1991 | Borie et al. ..................... | 53/127 |
| 5,047,211 A * | 9/1991 | Sloane et al. ................ | 73/64.41 |
| 6,103,518 A | 8/2000 | Leighton | |
| 6,162,399 A | 12/2000 | Martinell Gisper-Sauch | |
| 2003/0136813 A1 * | 7/2003 | Magerlein et al. .......... | 228/180.5 |
| 2006/0211080 A1 | 9/2006 | Frost, III et al. | |
| 2008/0169043 A1 * | 7/2008 | Osborne et al. ................... | 141/1 |

FOREIGN PATENT DOCUMENTS

EP    1466967 B1    10/2004

OTHER PUBLICATIONS

Spanish Search Report dated May 19, 2009.

* cited by examiner

*Primary Examiner* — Laura Martin
*Assistant Examiner* — Alex Devito
(74) *Attorney, Agent, or Firm* — RatnerPrestia

(57) ABSTRACT

Device for taking samples of liquid from a collection container, characterized in that it comprises a support for liquid sample collection containers; a support for a set of containers into which the sample of liquid will be deposited; a support for connection elements; a container handling mechanism; and a device for inserting the containers into which the sample of liquid will be deposited into the connection element.

40 Claims, 3 Drawing Sheets

DEVICE FOR THE AUTOMATIC TAKING OF SAMPLES OF LIQUID FROM COLLECTION CONTAINERS AND METHOD FOR PERFORMING SAID SAMPLE TAKING

The present invention relates to a device for the automatic taking of samples of liquid stored in collection containers and its labelling. More specifically, the present invention relates to the automatic taking of samples of any liquid, whether biological or nutritional, particularly blood or blood plasma. Moreover, the present invention also relates to the method for performing said sample taking from the collection containers.

Human plasma is the liquid part of blood and represents approximately 55% of total blood volume. It consists mainly of proteins and minerals, which are essential ingredients for the correct functioning of the body.

Various products may be obtained from the plasma taken by plasmapheresis, such as albumin, the use of which is very important in the treatment of liver and kidney diseases; gamma globulins, which are required for the treatment of numerous diseases; and coagulation factors, which are essential in the treatment of different types of haemophilia.

In general, the plasma is separated from the cellular component of the blood by means of plasmapheresis of the donor's blood immediately after it has been drawn. The plasma obtained by plasmapheresis is usually collected in closed plastic containers. After donation, a series of samples must be taken from the container which contains the plasma to carry out various analytical tests, mainly to determine the absence of infections.

At present, it is vitally important when working with containers for collecting liquids, to avoid the risk of mixing the containers in which the sample is taken. In addition, it is necessary to make absolutely certain that all the samples taken are from the same liquid collection container, which in the case of samples of blood or plasma corresponds to the same donor.

The plasma sample taking process is usually performed manually, there being a potential risk of mixing samples from different containers, despite the availability of standard working procedures to avoid such confusion.

An object of the present invention is to disclose a device for the automatic taking of samples from collection containers of a liquid, particularly human blood or plasma, using a system which may be open or closed. Moreover, an additional object of the present invention is that said device should label the containers in which the samples, which correspond unequivocally to the liquid collection container from which they were taken, are collected.

Another object of the present invention is to disclose a method of taking samples of liquid, which uses said device.

More particularly, the present invention relates to a device for taking samples of liquid, particularly human blood or plasma from a collection container, characterised in that it comprises:
- a support for the liquid collection containers;
- a support for a set of containers, or receiving containers into which the samples of liquid will be deposited;
- a support for elements connecting the containers;
- a mechanism for handling the containers into which the samples of liquid will be deposited;
- a device for inserting the containers into which the samples of liquid will be deposited, in the connection element.

Preferably, the liquid collection containers are bottles, bags or other suitable elements available on the market.

Also preferably, the containers into which the samples of liquid will be deposited will be vacuum containers or vacuum tubes, or any similar commercially available container.

Preferably the mechanism for handling the vacuum containers comprises a robot for transferring the vacuum containers into which the samples of liquid will be deposited.

Also preferably, the robot which handles the vacuum containers into which the sample of liquid will be deposited comprises terminals in any form which allow the vacuum containers to be grasped. Preferably said terminals are in the form of pincers.

In the device according to the present invention the feeding of the liquid collection containers, the connection elements and the containers into which the sample of liquid will be deposited may be carried out both manually and automatically. The automatic feeding process may be performed using conveyor belts, vibrators, stepped sliding plate feeders or any of the devices available on the market which are suitable for said supply process.

Also preferably the device comprises a zone which comprises a head for labelling the vacuum containers in which the label is printed and dispensed or simply dispensed.

Cannulas, needles, catheters or other suitable elements available on the market may be used as elements for connecting the liquid collection containers and the sample receiving containers in the device according to the present invention. Preferably, the connection element is a cannula.

Similarly, the labels used on the sample receiving containers of the device according to the present invention may be printed, of the RFID type or any other type of label available on the market. Preferably, the label used in the device according to the present invention is a printed label.

The liquid stored in the collection container may be a biological or nutritional liquid, or any other type of liquid. Preferably, the liquid is blood or blood plasma.

The device may also comprise a support for the vacuum containers which comprises a zone for placing the vacuum containers before the sample is deposited and another delivery zone for placing the vacuum containers, already full, which is different from the retrieval zone for empty sample containers.

Similarly, the device according to the present invention may comprise a zone for an additional support for vacuum containers, already full, which is different from the zone for the support of the empty containers.

The supports for the collection containers, the sample containers and the connection elements may be fixed in or removable from the device according to the present invention. Preferably, all the supports are removable.

Preferably, the device to insert the vacuum containers is capable of rotating about an axis and/or making linear movements, and also comprises terminals of any form which allow the vacuum packs to be grasped. Preferably, the insertion device comprises terminals in the form of pincers.

To identify the samples, the device comprises one or more readers of the labels of the liquid collection containers. The device may also comprise a labelling station for printing and dispensing or simply for dispensing the label on the sample containers.

Preferably, the device according to the present invention also comprises one or more readers of the labels of the containers into which the sample of liquid will be deposited.

The device according to the present invention may also comprise a collection zone for the sample containers in the form of a container or tray. It may further comprise one or more rejection zones for setting aside/separating the containers in which the sample will be or has been collected which are not of the required quality. This rejection zone may be suitable for classifying the type of rejection.

The present invention also relates to a method comprising the following steps:
- reading by means of a label reader of the collection container label;
- movement of the robot to the vacuum container support;
- retrieving a vacuum container by means of a retrieval terminal of the robot;
- transferring the retrieved container to the labelling station for printing and dispensing or simply dispensing a label on the vacuum container;
- transferring the vacuum tube to an insertion device for vacuum containers;
- rotation and/or linear movement of the insertion device for inserting the sample tube into the connection element, causing the liquid contained in the collection container to flow into the sample tube;
- removal of the full sample tube by means of a linear movement and/or rotation of the insertion device about an axis;
- transfer of the full vacuum tube from the insertion device to the support for full vacuum containers.

The robot may transfer the vacuum tube to another support for full vacuum containers.

The use of the device disclosed in the present invention has the additional advantages of guaranteeing the traceability of the samples, reducing the sample taking time and making it easier for the operator to handle the samples.

For a better understanding of the present invention, the accompanying drawings show a device for automatically taking samples of liquid according to the present invention, as an explanatory and non-limiting example.

DETAILED DESCRIPTION OF THE INVENTION

The present invention will be described based on an example of an embodiment, but this does not constitute a limitation. An embodiment of the device for the automatic taking of samples of liquid according to the present invention comprises:
- a support -1- for the liquid collection containers;
- a support -3- for the vacuum containers -4- into which the sample of liquid will be deposited;
- a cannula support -7-;
- a device -8- for inserting the vacuum containers in the cannula;
- a robot -9- for transferring the vacuum containers;
- a head -11- for labelling the vacuum containers, which in this case also includes a reading head -111- for reading the labels of the vacuum tubes.
- in addition, the device shown in the example also comprises a reader -13- for the label -21- of the liquid collection container -2-.

Figure 1:
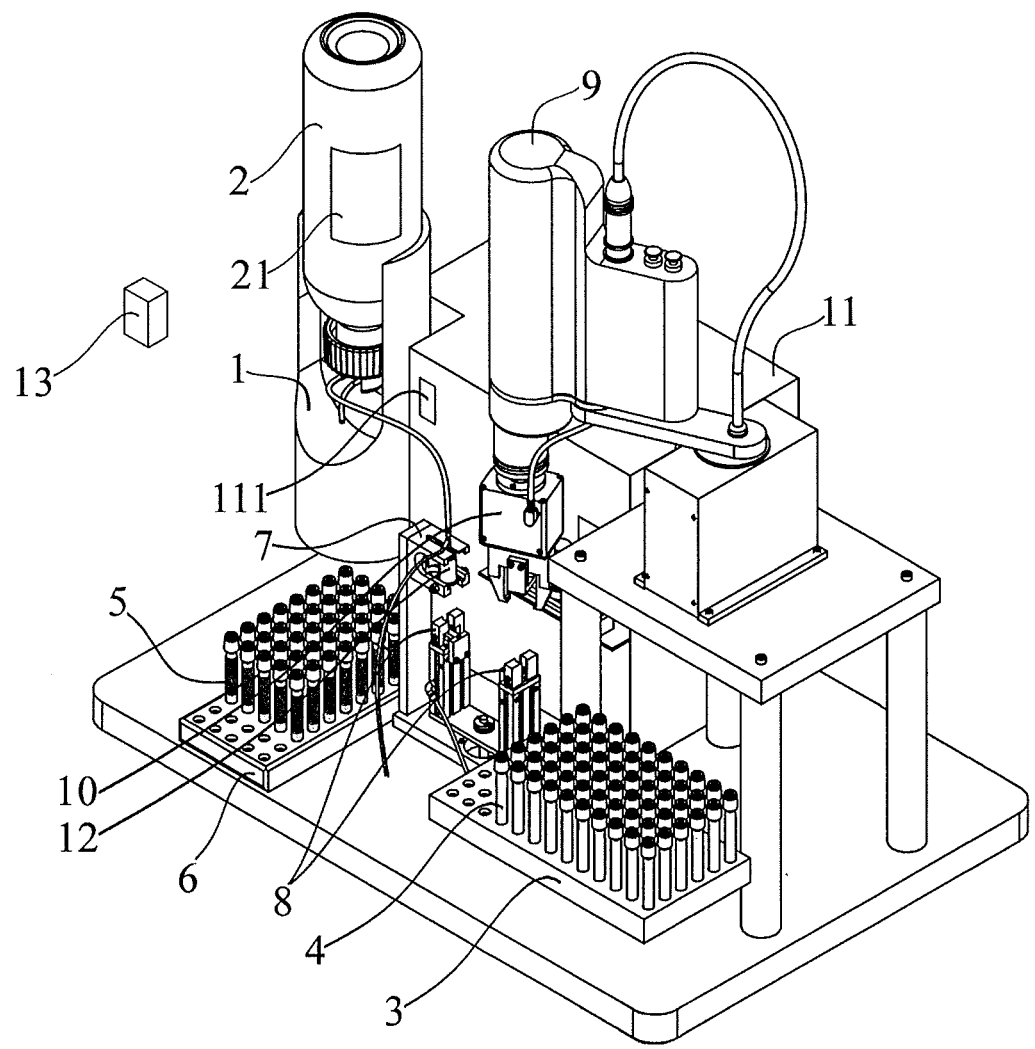
FIG. 1 shows a perspective view of the complete device for performing the present invention.

FIG. 1 shows a perspective view of the device according to the present invention in its entirety. The device comprises a support -1- for a liquid collection container -2-. The liquid collection containers -2- may, for example, be any of those available commercially on the market and must be suitable for being attached by means of needles, cannulas or other elements to the containers in which the sample will be collected. The liquid collection containers are placed in the device manually by the operator.

The device also comprises a support -3- for the vacuum containers -4-, into which the sample of liquid will be deposited from the liquid collection containers -2-. Preferably, the support -3- for the vacuum containers comprises a zone in which the vacuum containers remain before the sample is deposited and another zone for the vacuum containers already full. Optionally, the device may comprise another support -6- in which the full vacuum containers -5- are placed. The vacuum containers used may, for example, be any of those available commercially on the market.

The device also comprises a support -7- for the connection elements into which for example a cannula -12- for example of any type available commercially on the market may be fitted manually or automatically and attached to the liquid collection container -2-, also manually or automatically.

The device according to the present invention also comprises a device -8- for inserting the vacuum containers on the cannula. Said insertion device has the ability to rotate about an axis and/or perform linear movements and comprises pincers which are used to grasp the vacuum containers.

Further, the device comprises a robot -9-, which serves to automatically transfer the vacuum containers from the support -3- for the vacuum containers to the device -8- for inserting the vacuum containers and to transfer full tubes from the insertion device to the full tube support -6-, once the vacuum containers have been filled with liquid. Said robot -9- comprises in its lower portion a terminal in the form of a pincer -10- for grasping the vacuum containers.

A preferred embodiment of the device according to the present invention comprises a labelling zone, in which the label is printed and dispensed. This zone further comprises a head -11- for labelling the vacuum containers into which the sample of liquid will be deposited.

Figure 2:
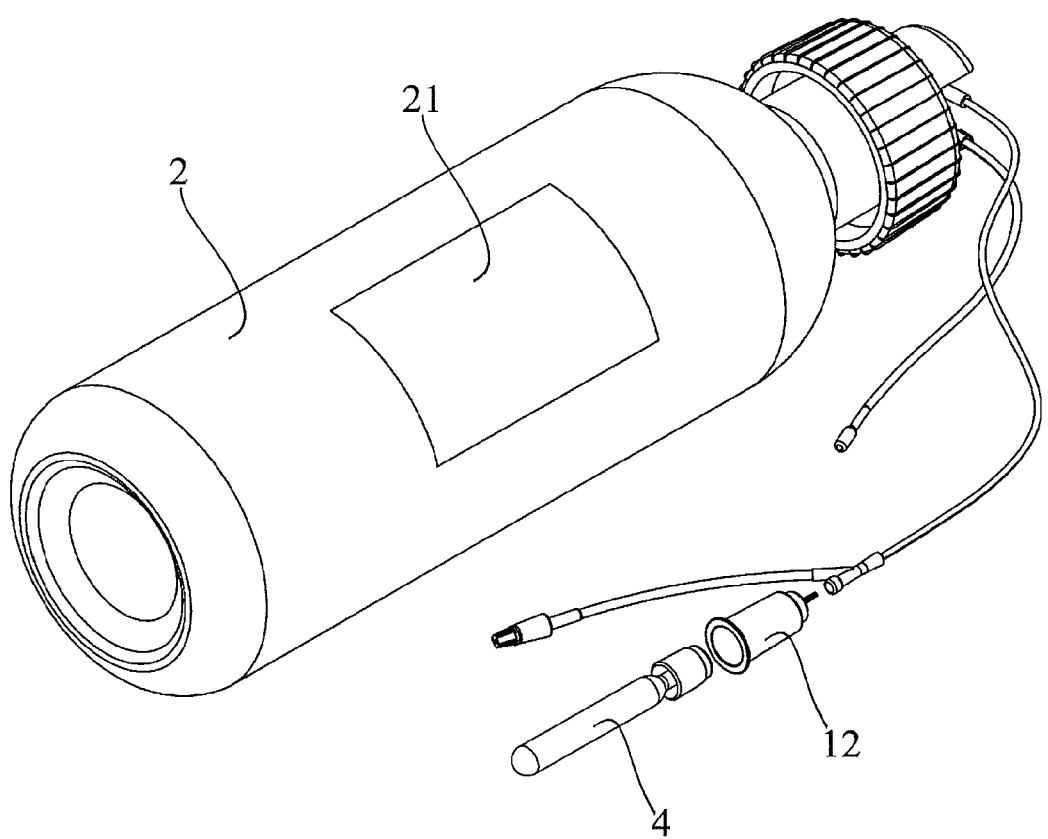
FIG. 2 shows a perspective view of the container which contains the liquid from which the sample will be deposited, the cannula and the vacuum tube used in the device according to the present invention.
Figure 3:
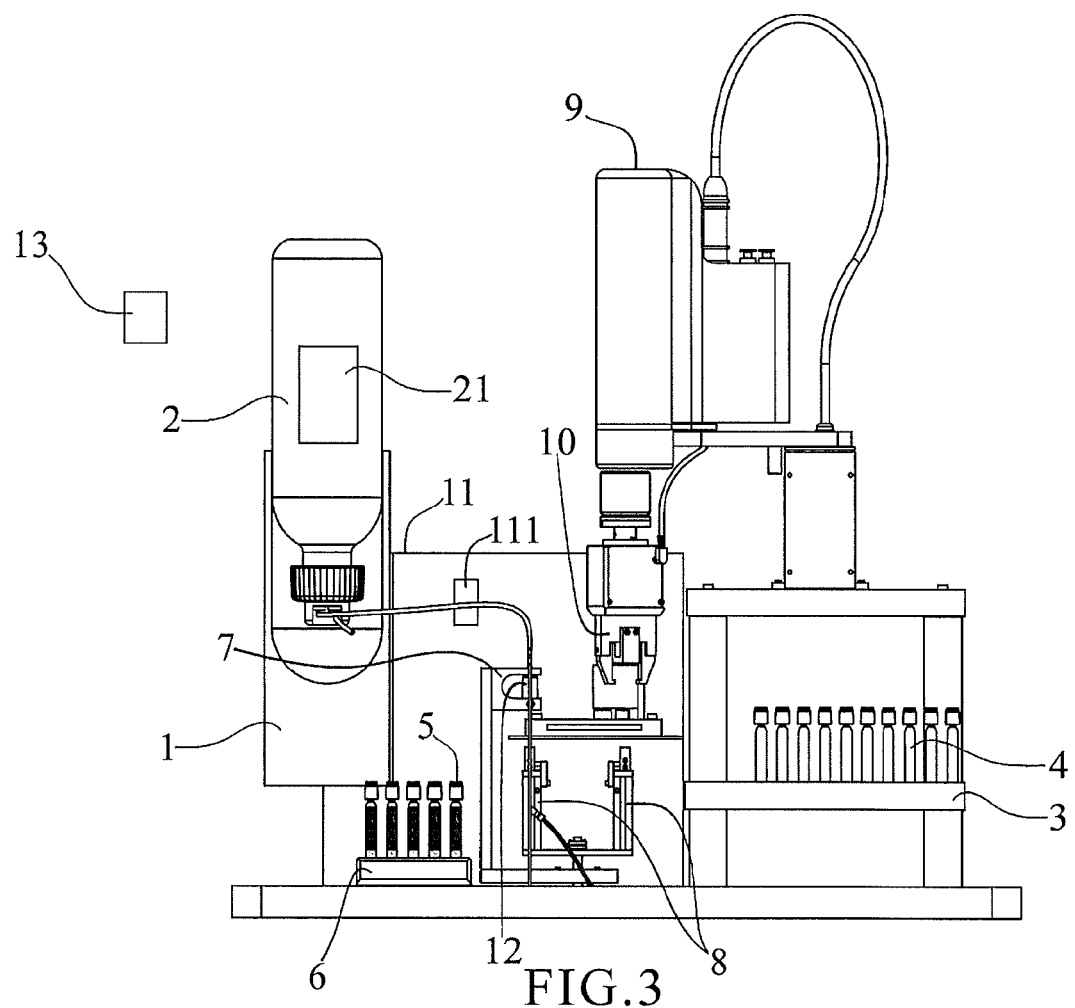
FIG. 3 shows a view in front elevation of the device according to the present invention.

FIG. 2 shows a liquid collection container -2-, a cannula -12- and a vacuum tube -4-, before being attached to take the sample of liquid.

The present invention also discloses a method for automatically depositing liquid from liquid collection containers into vacuum containers, using the device according to the present invention.

Once the operator has placed the liquid collection container -2- and the cannula -12- in position attaching them, and has also placed the vacuum containers -4- in position, the label reader -13- of the device according to the present invention automatically reads the label which has been adhesively bonded to the liquid collection container. Next, the robot -9- rotates to the vacuum container support -3-, retrieves one by means of its terminal in the form of pincers -10- and transfers it to the labelling station for the label to be printed and dispensed or simply dispensed. The robot -9- transfers the labelled vacuum tube to the tube label reader -111- where the correct and legible printing of the label is checked automatically.

Next, the insertion device -8- for the vacuum containers rotates and inserts the vacuum tube -4- into the cannula -12- causing the liquid contained in the collection container -2- to flow into the vacuum tube -4-. Next, the insertion device -8- removes the full vacuum tube from the cannula and rotates about its axis, and then the robot -9- transfers the full vacuum tube from the insertion device -8- to the full container support -6-, in the portion where the full and labelled vacuum containers are situated. Optionally, the robot -9- may transfer the full vacuum tube to a different support for full vacuum containers or to a rejection point/zone.

In a preferred embodiment of the present invention, when the automatic sample taking process is complete, the cannula is automatically expelled from the device.

In a particular embodiment of the method according to the present invention the handling mechanism may perform the functions of the insertion device. In addition, preferably in the method described, the device may handle more than one liquid collection container at a time. Further, the device may handle one or more connection elements at a time.

In another preferred embodiment, the device may reject the connection elements used and/or deform them so that they cannot be reused. Moreover, the device according to the present invention may comprise elements which check that the collection container and the connection element have been changed before carrying out a new sampling process from a different collection container. The connection between the collection container and the connection element may be made manually or automatically. The label of the collection container may also be read manually or automatically.

In another preferred embodiment of the method according to the present invention the device may handle the sample containers in a vertical or horizontal position; the handling mechanism and the insertion device may also retrieve/handle more than one sample container at a time.

The system may also include a rejection station for:
unlabelled vacuum packs
labelled vacuum packs
full, labelled tubes, etc.

It is also possible to program the system in such a way that the robot also performs the tasks of the insertion device.

Both the retrieval of the sample containers and the rejection may be performed using supports, trays, buckets or any container suitable for this function.

Although the invention has been described with regard to examples of preferred embodiments, said embodiments should not be considered to limit the invention, which will be defined by the widest interpretation of the following claims.

The invention claimed is:

1. A device for taking samples of liquid from a collection container, comprising:
    a plurality of sample receiving containers;
    a support for the plurality of sample receiving containers into which the sample of liquid will be deposited;
    a plurality of liquid collection containers, wherein each liquid collection container comprises a connection element having a first end connected to the liquid collection container and a second end for connecting to a sample receiving container;
    a support for the liquid collection containers;
    a support for the connection elements;
    a handling mechanism for the sample receiving containers; and
    a device for inserting the connection elements into the sample receiving containers.

2. The device according to claim 1, wherein the handling mechanism for the sample receiving containers comprises a robot for transferring the sample receiving containers.

3. The device according to claim 1, wherein the supply of liquid collection containers, connection elements and the containers into which the sample of liquid will be deposited is performed automatically.

4. The device according to claim 1, further comprising a zone which comprises a head for labelling the containers into which the sample of liquid will be deposited and in which the label is printed and/or dispensed or simply dispensed.

5. The device according to claim 1, wherein the elements for connecting the liquid collection containers and the sample containers are cannulas, needles, or catheters.

6. The device according to claim 1, wherein the element for connecting the liquid collection containers and the sample containers is a cannula.

7. The device according to claim 1 wherein the liquid collection containers are bottles or bags.

8. The device according to claim 1, wherein the containers into which the sample of liquid is deposited are vacuum containers or vacuum tubes.

9. The device according to claim 1, wherein labels are used on the sample containers that are printed and/or of the RFID type.

10. The device according to claim 9, wherein the labels used on the sample containers are printed.

11. The device according to claim 1, wherein labels are used on the collection containers that are printed and/or of the RFID type.

12. The device according to claim 11, wherein the labels used on the collection containers are printed.

13. The device according to claim 1, wherein the handling mechanism which handles the sample receiving containers comprises terminals of any form which allows the containers to be grasped.

14. The device according to claim 1, wherein the handling mechanism for the sample receiving containers comprises terminals in the form of pincers.

15. The device according to claim 1, wherein the insertion device which handles the sample receiving containers comprises terminals in any form which allows the containers to be grasped.

16. The device according to claim 1, wherein the insertion device which handles the sample receiving containers comprises terminals in the form of pincers.

17. The device according to claim 1, wherein the liquid in the collection container is a biological or nutritional.

18. The device according to claim 1, wherein the liquid in the collection container is blood or blood plasma.

19. The device according to claim 1, wherein the support for the sample containers comprises a zone for placing the sample containers before the sample is deposited and another zone for the full sample containers.

20. The device according to claim 1, wherein it comprises a zone for an additional support for the full sample containers which is different from the zone for the support for the empty sample containers.

21. The device according to claim 1, wherein each of the supports for the collection containers, the sample containers and the connection elements are fixed to the device or can be removed from said device.

22. The device according to claim 1, wherein the supports for the collection containers, the sample containers and the connection elements can be removed from said device.

23. The device according to claim 1, wherein it comprises one or more readers for the labels of the liquid collection container.

24. The device according to claim 9, wherein it comprises one or more readers for the labels of the sample receiving containers.

25. The device according to claim 1, wherein it comprises a delivery zone for full sample containers which is different from a retrieval zone for empty sample containers.

26. The device according to claim 1, wherein it comprises one or more rejection zones for a sample that is not of a specified quality.

27. A method for automatically taking samples of liquid using the device according to claim 1, wherein it comprises the following steps:
- reading by a label reader of a label on a collection container;
- movement of the handling mechanism to the sample container support;
- retrieving a sample container by means of a retrieval terminal of the handling mechanism;
- transfer of the retrieved container to the labelling station for a label to be printed and dispensed or simply dispensed on the sample container;
- transfer of the sample container to an insertion device of the sample containers;
- rotation and/or linear movement of the insertion device for inserting the connection element into the sample container, causing the liquid contained in the collection container to flow into the sample container;
- removal of the full sample container by the linear movement and/or rotation of the insertion device about an axis;
- transfer of the sample container from the insertion device to the sample container support.

28. The method according to claim 27, wherein the handling mechanism transfers the sample container to another support for full sample containers.

29. The method according to claim 27, wherein the handling mechanism performs the functions of the insertion device.

30. The method according to claim 29, wherein the insertion device performs the rotation and/or linear displacement movements.

31. The method according to claim 27, wherein the device may handle more than one liquid collection container at a time.

32. The method according to claim 27, wherein the device may handle one or more connection elements at a time.

33. The method according to claim 27, wherein the device may reject the connection elements used and/or deform them so that they cannot be reused.

34. The method according to claim 27, wherein the device comprises elements which check that the collection container and the connection element have been changed before carrying out a new sampling process from a different collection container.

35. The method according to claim 27, wherein the connection between the collection container and the connection element is made automatically.

36. The method according to claim 27, wherein the label of the collection container is read automatically.

37. The method according to claim 27, wherein the device may handle sample containers in a vertical or horizontal position.

38. The method according to claim 27, wherein the handling mechanism and the insertion device retrieve/handle one or more sample containers at a time.

39. The method according to claim 27, wherein the sample containers are retrieved using supports, trays, or buckets.

40. The method according to claim 27, wherein the sample containers are rejected using supports, trays, or buckets.

* * * * *